US009326765B2

(12) United States Patent
Lane et al.

(10) Patent No.: US 9,326,765 B2
(45) Date of Patent: May 3, 2016

(54) SUTURING DEVICE HAVING AN INTERNAL SUTURE DISPENSING MECHANISM

(71) Applicant: SafePath Medical, Inc., Methuen, MA (US)

(72) Inventors: Joseph P. Lane, Methuen, MA (US); Michael W. Sutherland, Pelham, NH (US)

(73) Assignee: SAFEPATH MEDICAL, INC., Amesbury, MA (US)

( * ) Notice: Subject to any disclaimer, the term of this patent is extended or adjusted under 35 U.S.C. 154(b) by 40 days.

(21) Appl. No.: 13/774,473

(22) Filed: Feb. 22, 2013

(65) Prior Publication Data
US 2013/0245646 A1 Sep. 19, 2013

Related U.S. Application Data

(60) Provisional application No. 61/602,052, filed on Feb. 22, 2012.

(51) Int. Cl.
*A61B 17/04* (2006.01)
*A61B 17/06* (2006.01)
*A61B 17/062* (2006.01)

(52) U.S. Cl.
CPC ......... *A61B 17/0493* (2013.01); *A61B 17/0467* (2013.01); *A61B 17/0491* (2013.01); *A61B 17/062* (2013.01); *A61B 17/06123* (2013.01); *A61B 2017/061* (2013.01); *A61B 2017/0608* (2013.01)

(58) Field of Classification Search
USPC .................................................. 606/145, 146
See application file for complete search history.

(56) References Cited

U.S. PATENT DOCUMENTS

| 2,336,690 A | 12/1943 | Karle |
| 4,373,530 A | 2/1983 | Kilejian |
| 4,406,237 A | 9/1983 | Eguchi et al. |
| 4,414,908 A | 11/1983 | Egochi et al. |
| 4,621,640 A | 11/1986 | Mulhollan et al. |
| 4,935,027 A * | 6/1990 | Yoon ............................. 606/146 |
| 4,957,498 A * | 9/1990 | Caspari et al. ................ 606/146 |
| 5,234,443 A | 8/1993 | Phan et al. |
| 5,437,681 A | 8/1995 | Meade et al. |
| 5,499,990 A | 3/1996 | Schülken et al. |
| 5,571,090 A | 11/1996 | Sherts |
| 5,571,119 A * | 11/1996 | Atala ............................ 606/146 |

(Continued)

FOREIGN PATENT DOCUMENTS

GB 630693 * 10/1949

OTHER PUBLICATIONS

U.S. Appl. No. 12/833,006, filed Jul. 9, 2011, McClurg et al.

*Primary Examiner* — Tuan V Nguyen
(74) *Attorney, Agent, or Firm* — Leason Ellis LLP

(57) ABSTRACT

A device for suturing tissue includes a handle that has a proximal end and a distal end. The device also includes a generally hollow suturing needle including a pointed distal end, an opposite proximal end and an inner lumen having an suture exit port through which the suture exits. The device further includes a suture dispensing mechanism disposed within the handle and including an actuator which when manipulated by a user is configured to advance suture material within the handle such that the suture material is guided into the inner lumen of the hollow suturing needle and exits through the suture exit port. The device includes a safety mechanism that shields at least a portion of the needle.

14 Claims, 14 Drawing Sheets

(56) References Cited

U.S. PATENT DOCUMENTS

| | | | |
|---|---|---|---|
| 5,609,597 | A | 3/1997 | Lehrer |
| 5,643,292 | A | 7/1997 | Hart |
| 5,665,109 | A | 9/1997 | Yoon |
| 5,709,693 | A | 1/1998 | Taylor |
| 5,728,113 | A | 3/1998 | Sherts |
| 5,730,747 | A | 3/1998 | Ek et al. |
| 5,746,751 | A | 5/1998 | Sherts |
| 5,759,188 | A | 6/1998 | Yoon |
| 5,766,186 | A | 6/1998 | Faraz et al. |
| 5,824,009 | A | 10/1998 | Fokuda et al. |
| 5,843,100 | A | 12/1998 | Meade |
| 5,860,992 | A | 1/1999 | Daniel et al. |
| 5,871,488 | A | 2/1999 | Tovey et al. |
| 5,904,692 | A * | 5/1999 | Steckel et al. ............... 606/139 |
| 5,908,428 | A | 6/1999 | Scirica et al. |
| 5,919,202 | A | 7/1999 | Yoon |
| 5,935,149 | A | 8/1999 | Ek |
| 5,951,575 | A | 9/1999 | Bolduc et al. |
| 5,954,733 | A | 9/1999 | Yoon |
| 5,957,937 | A | 9/1999 | Yoon |
| 5,984,932 | A | 11/1999 | Yoon |
| 5,993,466 | A | 11/1999 | Yoon |
| 5,993,467 | A | 11/1999 | Yoon |
| 6,048,351 | A | 4/2000 | Gordon et al. |
| 6,071,289 | A | 6/2000 | Stefanchik et al. |
| 6,099,550 | A | 8/2000 | Yoon |
| 6,099,553 | A | 8/2000 | Hart et al. |
| 6,159,224 | A | 12/2000 | Yoon |
| 6,224,614 | B1 | 5/2001 | Yoon |
| 6,277,132 | B1 | 8/2001 | Brhel |
| 6,533,795 | B1 | 3/2003 | Tran et al. |
| 6,911,034 | B2 | 6/2005 | Nobles et al. |
| 6,923,819 | B2 | 8/2005 | Meade et al. |
| 6,984,237 | B2 | 1/2006 | Hatch et al. |
| 6,997,932 | B2 | 2/2006 | Dreyfuss et al. |
| 7,011,668 | B2 | 3/2006 | Sancoff et al. |
| 7,033,370 | B2 | 4/2006 | Gordon et al. |
| 7,060,077 | B2 | 6/2006 | Gordon et al. |
| 7,090,686 | B2 | 8/2006 | Nobles et al. |
| 7,108,700 | B2 | 9/2006 | Chan |
| 7,316,694 | B2 | 1/2008 | Reinitz |
| 7,326,221 | B2 | 2/2008 | Sakamoto et al. |
| 7,331,970 | B2 | 2/2008 | Almodovar |
| 7,338,504 | B2 | 3/2008 | Gibbens et al. |
| 7,442,198 | B2 | 10/2008 | Gellman et al. |
| 7,544,199 | B2 | 6/2009 | Bain et al. |
| 7,572,265 | B2 | 8/2009 | Stone et al. |
| 7,582,096 | B2 | 9/2009 | Gellman et al. |
| 7,588,583 | B2 | 9/2009 | Hamilton et al. |
| 7,615,059 | B2 | 11/2009 | Watschke et al. |
| 7,628,796 | B2 | 12/2009 | Shelton et al. |
| 7,704,262 | B2 * | 4/2010 | Bellafiore et al. ............ 606/144 |
| 7,998,149 | B2 | 8/2011 | Hamilton et al. |
| 8,172,860 | B2 * | 5/2012 | Zung et al. .................... 606/144 |
| 8,252,007 | B2 | 8/2012 | Hamilton et al. |
| 8,257,371 | B2 | 9/2012 | Hamilton et al. |
| 8,317,805 | B2 | 11/2012 | Hamilton et al. |
| 8,419,754 | B2 | 4/2013 | Laby et al. |
| 8,603,113 | B2 | 12/2013 | Hamilton et al. |
| 8,617,187 | B2 | 12/2013 | Hamilton et al. |
| 8,685,045 | B2 | 4/2014 | Hamilton et al. |
| 2002/0087178 | A1 | 7/2002 | Nobles et al. |
| 2003/0023250 | A1 | 1/2003 | Watschke |
| 2004/0243147 | A1 | 12/2004 | Lipow |
| 2005/0043747 | A1 | 2/2005 | Field et al. |
| 2005/0085857 | A1 | 4/2005 | Peterson et al. |
| 2005/0119670 | A1 | 6/2005 | Kerr |
| 2005/0234479 | A1 | 10/2005 | Hatch et al. |
| 2005/0267529 | A1 | 12/2005 | Crockett et al. |
| 2006/0069396 | A1 | 3/2006 | Meade et al. |
| 2006/0282088 | A1 | 12/2006 | Ryan |
| 2007/0021755 | A1 | 1/2007 | Almodovar |
| 2007/0060930 | A1 | 3/2007 | Hamilton et al. |
| 2007/0060931 | A1 | 3/2007 | Hamilton et al. |
| 2007/0088372 | A1 | 4/2007 | Gellman et al. |
| 2007/0225735 | A1 | 9/2007 | Stone et al. |
| 2007/0270885 | A1 | 11/2007 | Weinert et al. |
| 2008/0243147 | A1 | 10/2008 | Hamilton et al. |
| 2008/0249545 | A1 | 10/2008 | Shikhman |
| 2009/0012538 | A1 | 1/2009 | Saliman et al. |
| 2009/0024145 | A1 | 1/2009 | Meade et al. |
| 2009/0157105 | A1 | 6/2009 | Zung et al. |
| 2009/0292300 | A1 | 11/2009 | Hamilton et al. |
| 2010/0010512 | A1 | 1/2010 | Taylor et al. |
| 2010/0016868 | A1 | 1/2010 | Kim |
| 2010/0030238 | A1 | 4/2010 | Viola et al. |
| 2010/0152751 | A1 | 6/2010 | Meade et al. |
| 2010/0268257 | A1 | 10/2010 | Hamilton et al. |
| 2010/0280530 | A1 | 11/2010 | Hashiba |
| 2011/0251627 | A1 | 10/2011 | Hamilton et al. |
| 2011/0313433 | A1 | 12/2011 | Woodard, Jr. et al. |
| 2012/0165837 | A1 | 6/2012 | Belman et al. |
| 2012/0316580 | A1 | 12/2012 | Belman et al. |
| 2013/0165954 | A1 * | 6/2013 | Dreyfuss et al. ............ 606/146 |
| 2013/0231687 | A1 | 9/2013 | Laby et al. |
| 2013/0304096 | A1 | 11/2013 | Nguyen et al. |
| 2014/0222036 | A1 | 8/2014 | Hamilton et al. |
| 2014/0276988 | A1 | 9/2014 | Tagge et al. |
| 2014/0288581 | A1 | 9/2014 | Hamilton et al. |

\* cited by examiner

SUTURING DEVICE HAVING AN INTERNAL SUTURE DISPENSING MECHANISM

CROSS-REFERENCE TO RELATED APPLICATION

The present application claims the benefit of U.S. patent application Ser. No. 61/602,052, filed Feb. 22, 2012, which is hereby incorporated by reference in its entirety.

TECHNICAL FIELD

The present invention relates to devices and methods for suturing tissue and more specifically, relates to a handheld device that includes a suturing needle, an internal suture dispensing mechanism, and a safety shield mechanism for shielding the suturing needle during the suturing operation.

BACKGROUND

Needles and suture are used throughout the healthcare industry for indications such as wound and incision closure, securing catheters, and affixing implantable meshes, annuloplasty rings, and other medical apparatus. These sutures are used on the surface of the patient's skin as well as through laparoscopic, endoscopic, and surgical procedures. Because needles represent injury and illness risks to the user, there is a need to make needle usage safer without sacrificing ease of use, performance, and cost. A medical device that can be used to safely suture the tissue of a patient will be valuable to physicians, surgeons, nurses, physician assistants, military personnel, and other clinical and non-clinical users of suture.

SUMMARY

A device for suturing tissue includes a handle that has a proximal end and a distal end. The device also includes a generally hollow suturing needle including a pointed distal end, an opposite proximal end and an inner lumen having a suture exit port through which the suture exits. The device further includes a suture dispensing mechanism disposed within the handle and including an actuator which when manipulated by a user is configured to advance suture material within the handle such that the suture material is guided into the inner lumen of the hollow suturing needle and exits through the suture exit port. A device also includes a safety mechanism that shields at least a portion of the needle.

The safety mechanism is pivotally attached to the handle and the device is configured to allow the user to manually pass the suturing needle through tissue at variable penetration depths by employing a rotational motion of the user's hand. In one embodiment, the suture dispensing mechanism includes a suture spool that contains wound suture material. The suture spool is operatively connected to the actuator whereby the manipulation of the actuator by the user is translated into rotation of the suture spool and the suture material is advanced within the handle, whereby continued rotation of the suture spool results in the suture material being guided into the inner lumen of the hollow suturing needle and exiting through the suture exit port.

Alternatively, the suture dispensing mechanism includes a pair of pinch rollers, one of which is operatively coupled to the actuator such that actuation of the actuator is translated into rotation of the one pinch roller. The suture material is fed between and is driven by rotation of the pinch rollers. In addition, the actuator includes an elongated extension that has a plurality of compliant angled fingers depending therefrom, and the suture dispensing mechanism includes an open guide channel member that has a channel through which the suture material passes. The compliant angled fingers are at least partially disposed within the channel to allow intimate contact between the fingers and the suture material. The actuator, including the extension, moves in a linear manner such that during each down stroke of the actuator, the fingers drive the suture material towards the needle, thereby advancing the suture material through the handle and needle.

These and other features will be appreciated in view of the following detailed description and the drawing figures.

BRIEF DESCRIPTION OF DRAWING FIGURES

Figure 1:
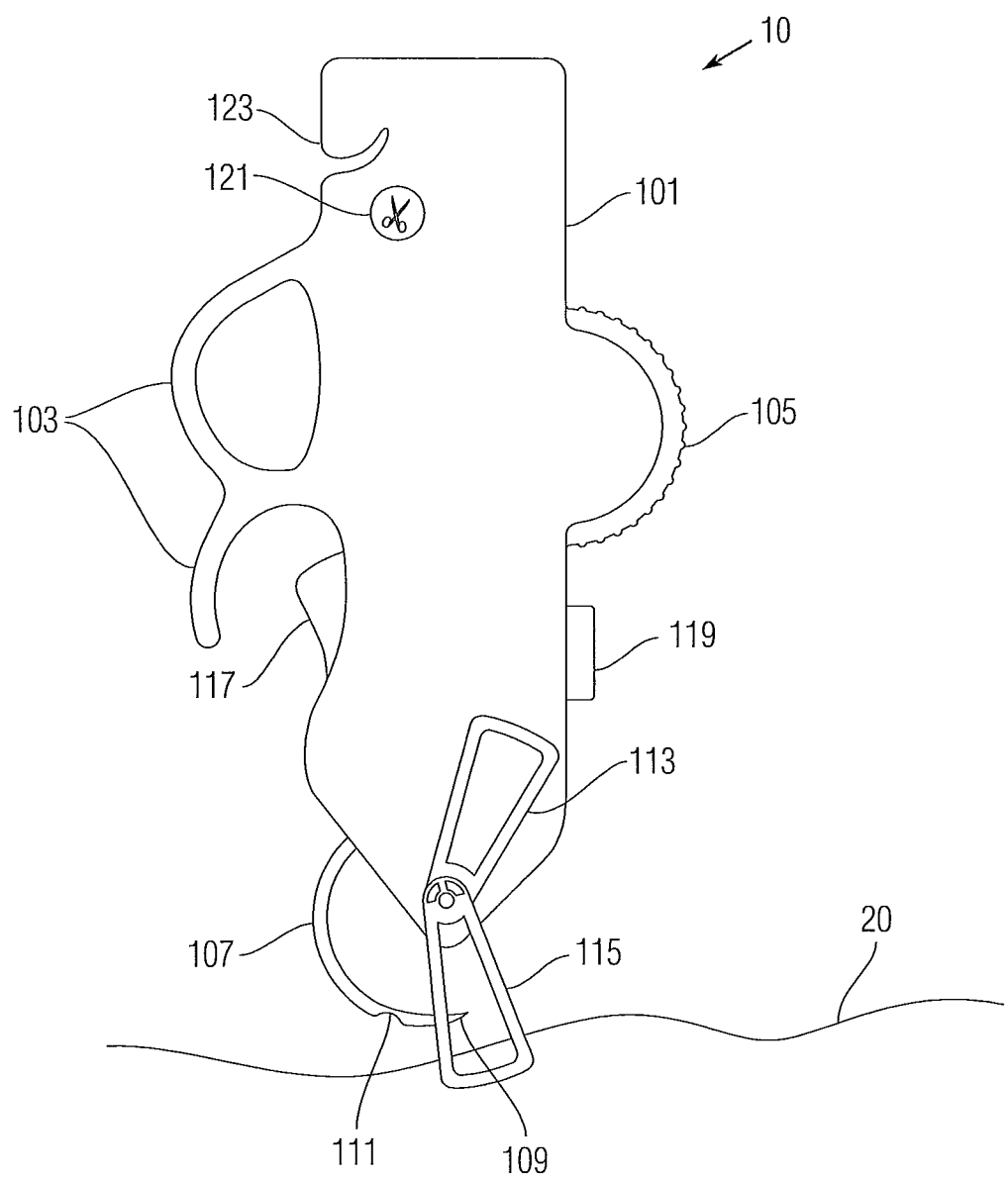
FIG. 1 is a side elevation view of a suturing device according to one exemplary embodiment and shown in a first position.
Figure 7:
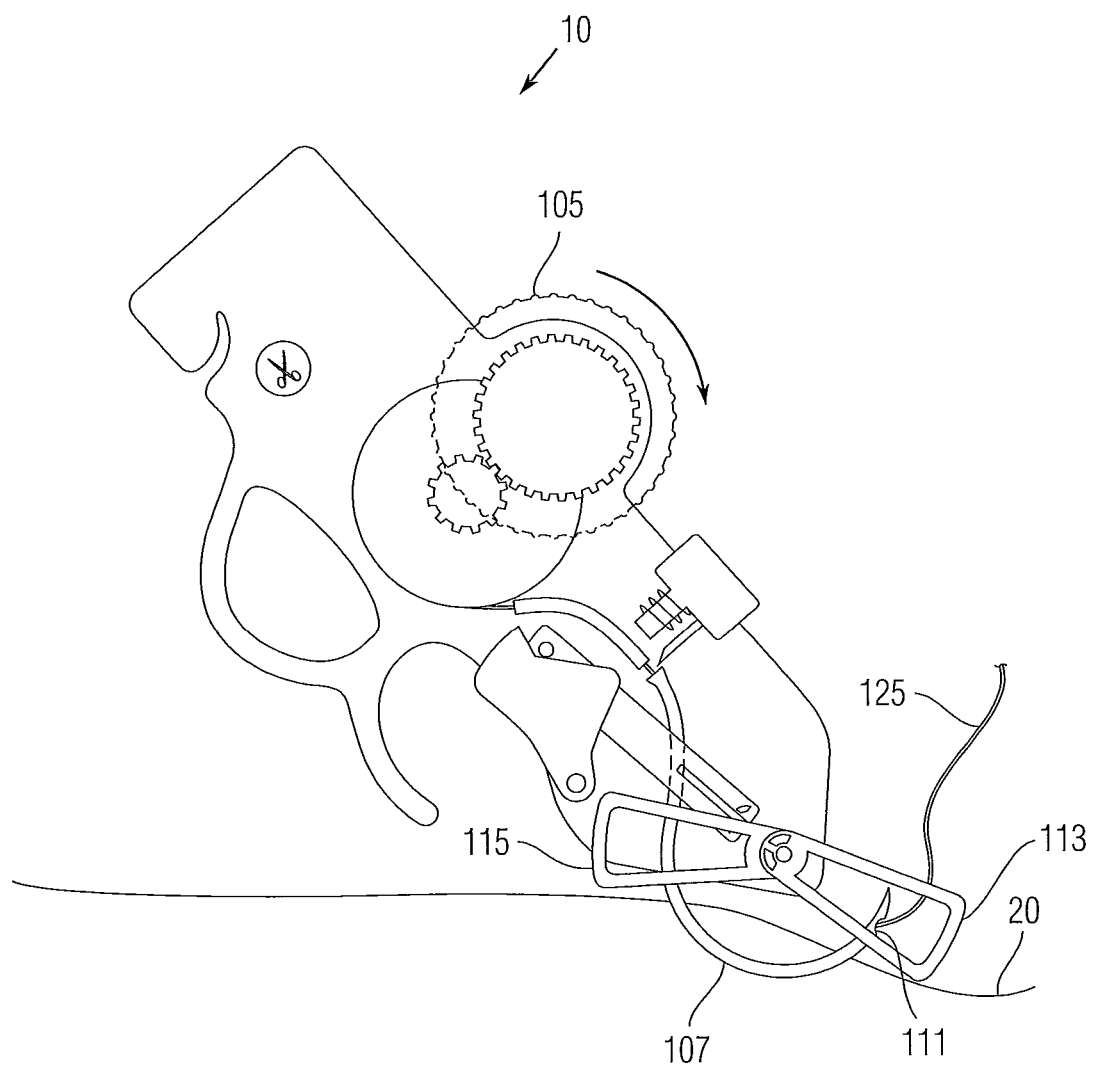
FIG. 7 is a cross-sectional view of the suturing device of FIG. 1 showing advancement of the suture through a hollow needle that has passed through tissue.
Figure 8:
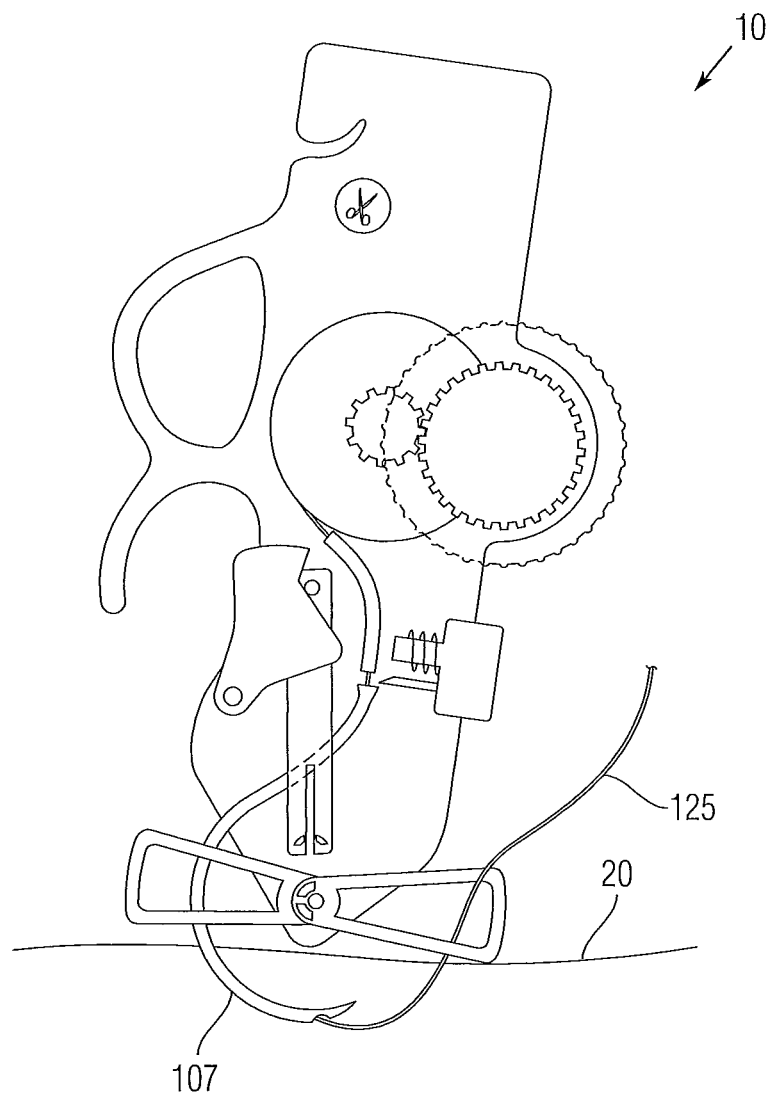
Figure 9:
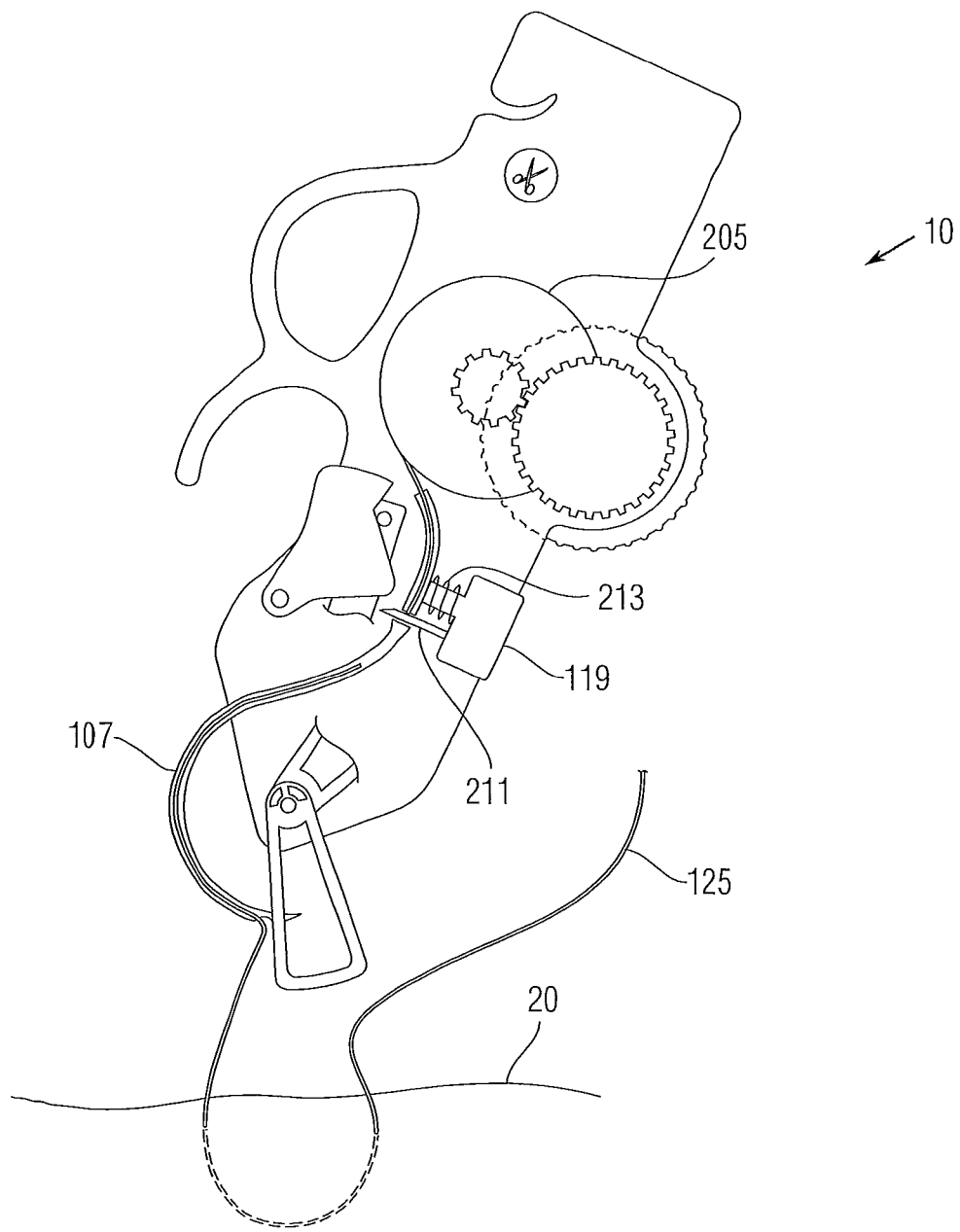
Figure 10:
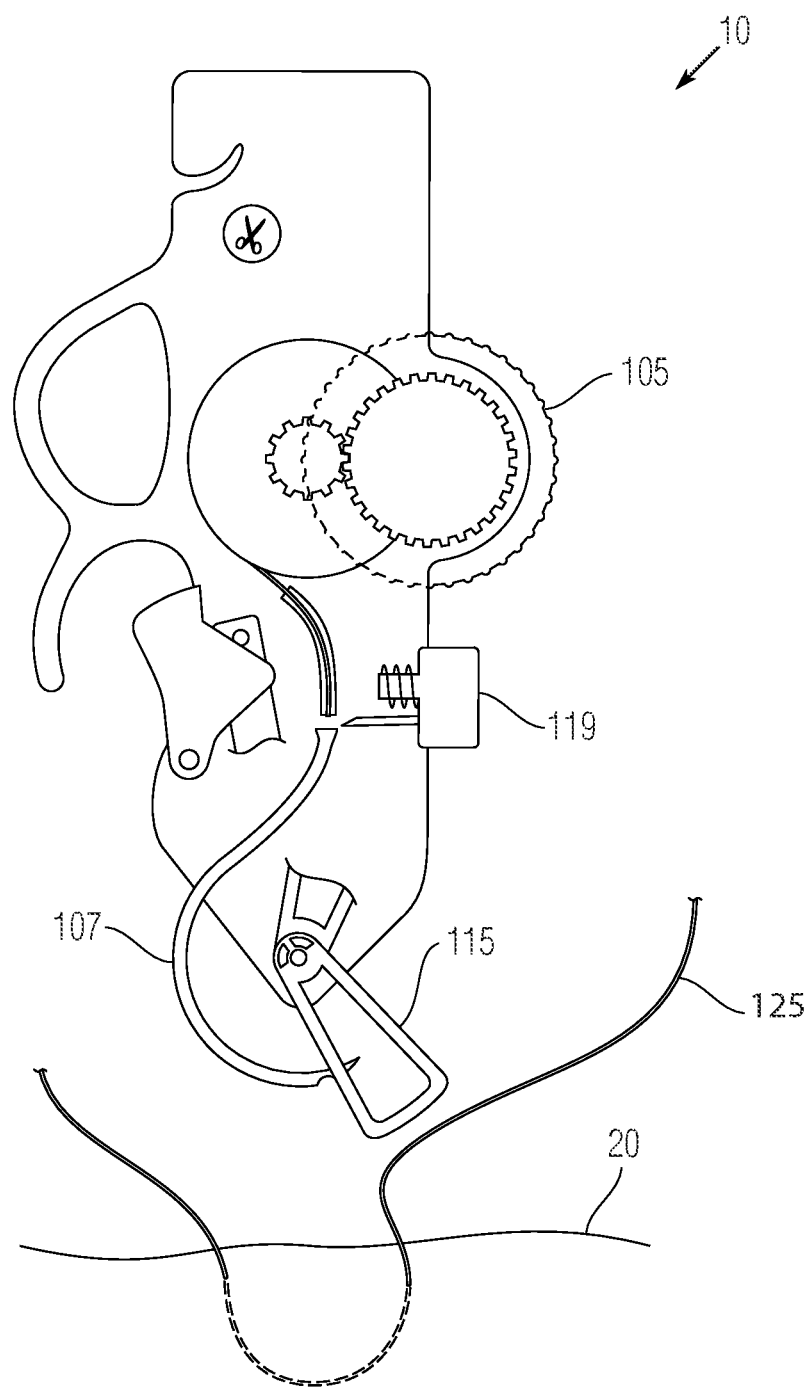
Figure 11:
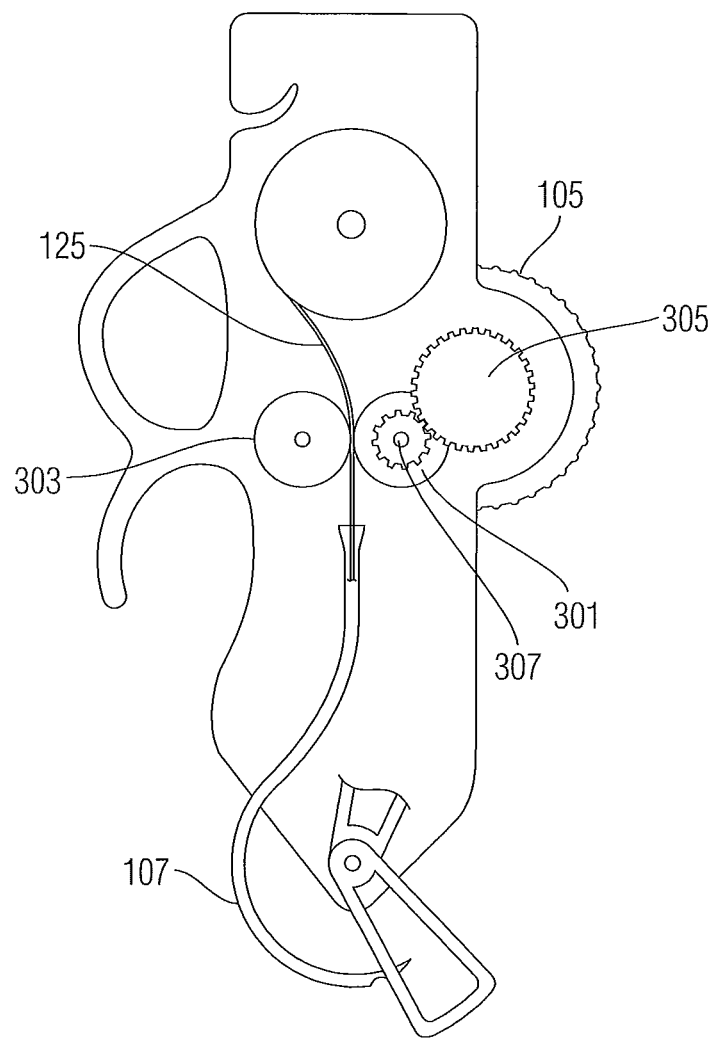
Figure 12:
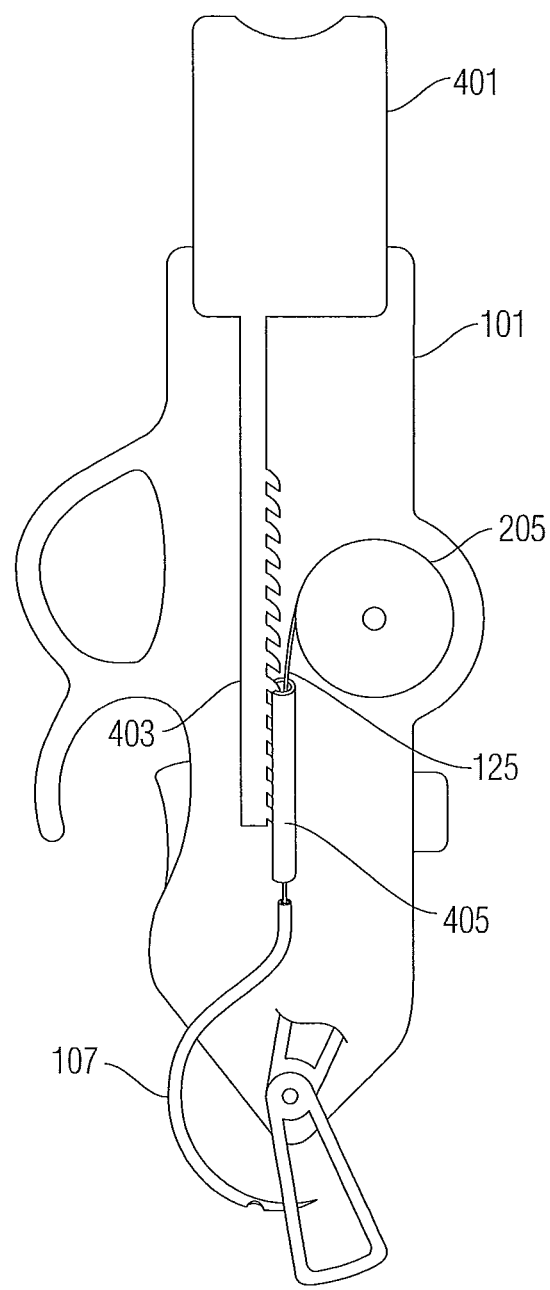
Figure 13:
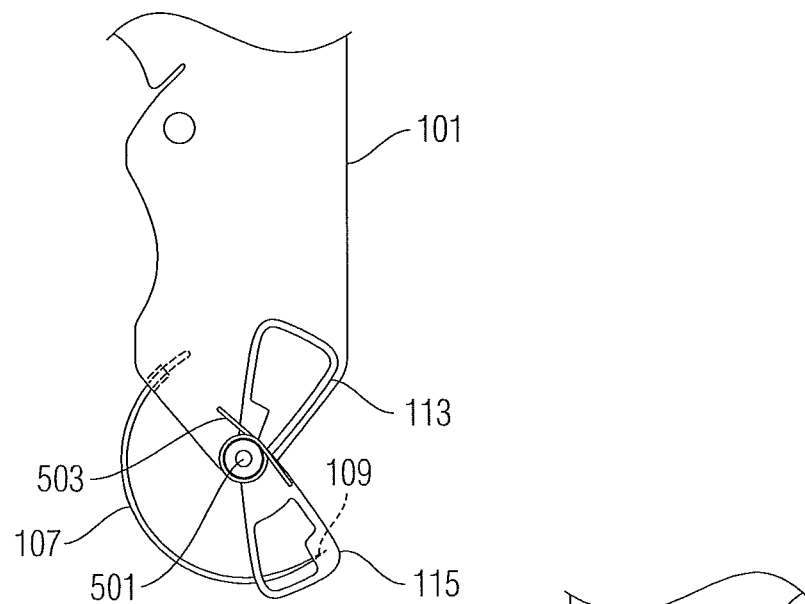
Figure 14:
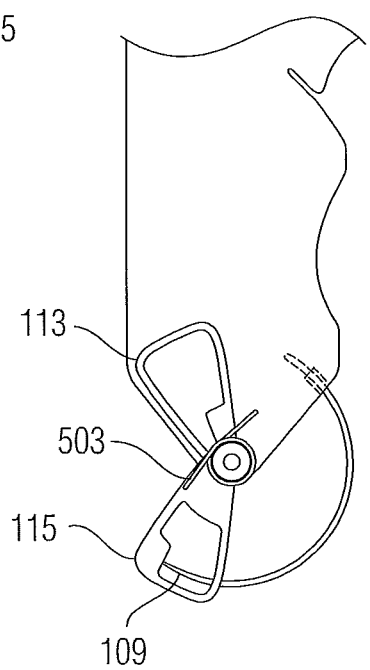
Figure 15:
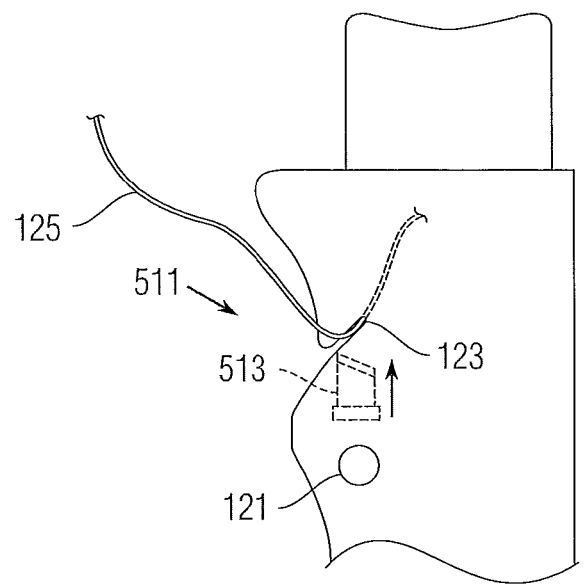
Figure 16:
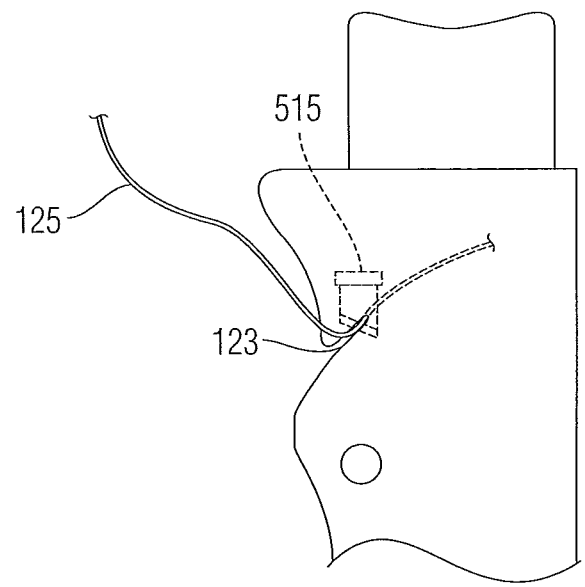

FIG. 8 a cross-sectional view of the suturing device of FIG. 7 showing rotation of the device after the suture has been advanced;

FIG. 9 is a cross-sectional view of the suturing device of FIG. 1 showing cutting of the advanced suture;

FIG. 10 a cross-sectional view of the suturing device of FIG. 1 showing removal of the device away from the cut suture;

FIG. 11 is a cross-sectional view of a suturing device according to another suture management embodiment;

FIG. 12 is a cross-sectional view of a suturing device according to another suture management embodiment;

FIG. 13 is a front elevation view of the distal end of the device showing a safety shield mechanism according to one exemplary embodiment according to one embodiment;

FIG. 14 is a rear elevation view of the distal end of the device showing the safety shield mechanism;

FIG. 15 is a partial side elevation view of the device showing an internal cutter mechanism according to one exemplary embodiment; and FIG. 16 is a partial side elevation view of the device showing an internal cutter mechanism according to another embodiment.

DETAILED DESCRIPTION OF THE PREFERRED EMBODIMENTS

Disclosed herein are device concepts and methods for safely suturing tissue, skin, muscle, ligament, tendon and similar structures throughout the entire body. Healthcare workers need a safe method and device for closing wounds and incisions, approximating tissue, securing meshes and annuloplasty rings, securing catheters to a patient, and related functions. The current procedure typically consists of a user grasping an unprotected needle and suture with hemostats, a needle driver, forceps, or suturing device and then piercing the patient's tissue by utilizing hand, wrist, and device movements. In this scenario, the needle point is exposed to the user before, during, and after the procedure and provides risk for accidental needle stick injuries (NSI) to the user and procedural staff. These NSIs can transmit bloodborne pathogens such as hepatitis and HIV to the user and others from the patient and potentially cause illness or death. Users that are injured in this manner are required to report the injury, undergo diagnostic tests and begin receiving prophylactic treatment. They may also be required to take a leave of absence from work or continue indefinitely with a prescribed drug regimen.

The device conceived herein is a compact, light-weight handheld device that comprises a hollow needle, a suture, a suture management mechanism, and safety apparatus, and that is capable of safely penetrating a patient's tissue and delivering one or more sutures for the purposes detailed above. The device accommodates the right or left-handed user without reconfiguration, rests comfortably in the user's hand, allows sufficient visualization of the procedure site, and permits the user to control penetration depth of the needle or default to a depth that is predetermined by the device. In one embodiment, this device permits the user to utilize a similar wrist-rotation suture delivery technique that is currently employed for securing a catheter, closing a wound, or for related suture-based procedures. In other embodiments, the device contributes part of the motion required to penetrate a patient's tissue.

In a preferred embodiment, the device has the following definitive advantages over current art: Safety: The user cannot contact the point of the needle and is able to avoid accidental NSIs and the human and financial costs associated with those accidents. Performance: The device allows the user to reproduce the needle delivery motion that is currently used by healthcare workers. This improves the accuracy and integrity of the securement and reduces the trauma to the patient. Size: The device is sized and oriented for easy access to crowded and narrow regions of the patient's body such as the neck; Ease of Use: The device can be generally operated with one hand, by right-handed and left handed users, and multiple sutures are able to be secured to the patient through a minimal series of steps. Cost: The device is designed as a single use device that is economical and easy to manufacture. Versatility: The device is suitable for use within a hospital environment and any first aid setting. It can be utilized to secure nearly every type of catheter and to close wounds. In addition, it may be packaged within catheter and medical accessory sets or as a stand-alone device.

In one exemplary embodiment, the needle within this device is hollow, rigidly attached to the device handle, and serves as a conduit for numerous varieties of suture and similarly configured materials after the needle crosses the patient's tissue. This allows the user to easily pass one or more sutures through the patient's tissue and, with the aid of safety features it protects the user from contact with the needle before, during, and after the procedure. At the conclusion of each suture delivery, the safety features are automatically locked and needle is safely shielded from the user. Additional elements within this embodiment include one or more integral cutters in order that the suture can be cut or trimmed by the user without the need for a separate scissors or scalpel.

Although it is contemplated as a single-use device, it is understood that slight alterations can be made to the design and materials that would allow said device to be resterilized, reloaded with an additional needle and suture, and reused. It may be further contemplated that the distally mounted needle has the ability to rotate relative to the handle and replicate the manual needle-driving motion of crossing tissue that is currently used in and outside the clinic. This is particularly useful in laparoscopic, endoscopic, and surgical procedures when the user's natural range of motion is compromised.

Looking again at the primary embodiment, the handle, which is comprised of one or more components such as a housing, actuators, and buttons, may be molded, cast or extruded from a variety of materials including but not limited to polymers or metals. Examples of polymers suitable for fabricating the handle are thermoplastic and thermosetting materials such as polystyrene, acrylic, polycarbonate, polyamide, polyester, polyetherimide, polysulfone, polylactic acid, polyvinylchloride, polyolefins, polyurethane, fluoropolymers, and copolymers and alloys thereof. These materials may be filled with glass or other useful reinforcing agents in order to enhance their mechanical properties. Suitable metals come from but are not limited to a group including titanium alloys and stainless steel. The selected materials must meet physical and mechanical performance requirements and be able to withstand sterilization methods employed within the medical device industry such as ethylene oxide or gamma irradiation. The handle design may be constructed to be linear and longitudinal, non-planar, angled, or a combination of these conformations.

The needle features a distal pointed end suitable for piercing and crossing tissue, a proximal end, a body between the distal and proximal ends, and a generally hollow cross-section suitable for guiding a suture therethrough. The needle can be fabricated in a variety of configurations such as straight, curved, non-planar, and/or a combination of these elements, and be monolithic, hollow or of a multi-part construction. Their outer diameters may be fabricated as round or non-round, tapered, or possesses features that assist in crossing tissue or prevent bending. Inner diameters are sufficiently large as to allow passage to suture or similarly configured materials, and may be present along the entire length of the needle or a portion(s) thereof. Needles are commonly made from stainless steel and related alloys but can be made from other metals, polymers and ceramic materials that are sufficiently rigid, capable of possessing and sustaining a functionally sharp distal point, and able to penetrate tissue without adversely yielding or bending. Coatings on the needle serve to enhance the lubricity of the needle and reduce tissue penetration forces. Longitudinal ribs or recessions or other features found on the inner diameter and/or outer diameter of the needle may provide additional rigidity and enhance the needle's ability to effectively cross tissue.

The suture is the thread-like material that is used to treat internal and external wounds and incisions and to secure catheters or other components to patients. It comes in a variety of diameters, textures, forms, i.e., single strand or braided, and materials depending upon the desired properties and intended application. Sutures can be absorbable, i.e., collagen, polyglactin, polydioxanone, polyglycolide-lactide copolymers, or non-absorbable, i.e., silk, nylon, polyester, polypropylene, stainless steel. They can be treated with antimicrobial, bioabsorbable, hydrophilic or other functional additives. In addition, they can have surface features that permit the suture to be drawn smoothly through tissue in one direction but snag the tissue when pulled in the opposite direction. This is advantageous when the user wants to temporarily or permanently approximate tissue without the need to tie a knot.

The suture described above is generally understood to be preloaded on an internal suture management system such as a spool, capstan, pulley, reel, or other means suitable for storing and dispensing suture. This component(s) serves to organize, release, clutch, and advance the suture into and through the generally hollow needle. The internal components are activated through features, i.e., wheel, dial, lever, slide, buttons and the like, which are manipulated by the user. Based on the device design, the spool may rotate either unidirectionally or bidirectionally. Alternatively, the suture may be loaded by the user into the device such that it travels into and through the needle.

Moreover, the safety apparatus, which protects the user from the needle point before, during, and after the procedure, can exist in numerous forms. It can comprise single or multiple components, be biased to a safety-mode position and/or be user actuated, and/or have reversible or irreversible lockout features. The apparatus may be configured, for example, as a slideable or rotatable cover, or as deflectable wing-like shields that obstruct user access to the needle point. Like the handle described above, the safety apparatus may be made from a wide range of thermoplastic and thermosetting polymers, however, a transparent polymer or a thin-wall construction may be superior as it would provide the user with greater visibility of the needle and suturing site. Furthermore, it may be manufactured from metals, such as stainless steel, titanium, and titanium alloys including nickel-titanium, and configured as a wire-form, mesh, grid, or strut. A spring or other force-resilient components may be incorporated in order to bias the safety apparatus into a safe position or to actuate multiple components that comprise the safety apparatus.

Referring to the lockout feature above, it will prevent the user from accidentally exposing the needle and obtaining an NSI. The lockout generally takes the form of a user-actuated button, lever, slide, or other similar means and a connecting element that couples the actuation means and the safety apparatus. At times, the actuation means and connecting element can be constructed as a single component. The button causes the connecting element to lock and unlock the apparatus in a variety of ways. Examples of these means include tongue and groove, intermeshing gears, friction and interference fits, inclined planes, cantilever, and screws. In each of these methods, the connecting element restricts the movement of the apparatus, and therefore, the exposure of the needle until the user actuates the button to release the apparatus.

Finally, one or more suture cutters are located within the device handle so that the user may trim knotted sutures and suture strands to length. The cutter is envisioned as a dynamic shearing apparatus, i.e., scissors or slideable blade(s) that would require the user to press or slide a button in order to actuate the blade to cut the suture. Alternatively, the cutter could be a simple apparatus such as a static cutting blade located in a narrowing, crevice-like feature on the handle. In this configuration, the suture could be drawn across the sharp edge of the blade in order to cut it. Typical materials that are useful as cutting blades are stainless steel, carbon steel, and gemstones, such as diamond. For safety purposes, the user does not have direct access to the cutting blade; only suture is able to reach the blade via the suture cutter notch or internal channel. Beyond the safety advantage, the integral cutters would reduce or eliminate the need for the user to provide a separate pair of scissors for cutting or trimming suture during the procedure.

The devices disclosed herein are related to those disclosed in commonly owned U.S. patent application Ser. No. 13/584, 536, filed Aug. 13, 2012, which is hereby incorporated by reference in its entirety.

Referring now to FIG. 1, a suturing device 10 according to one exemplary embodiment of the present invention is depicted. The device 10 features a handle 101 with an elongate body and a number of ergonomic gripping surfaces 103 suitable for both left and right-handed users. The elongate body houses the inner mechanisms of the device, which are not shown in FIG. 1. An actuation wheel or the like 105 is used to dispense suture (not shown in FIG. 1) and extends outwardly from the side of the device. Alternatively, the wheel could extend from the top of the device. The wheel 105 thus comprises an actuator that is readily accessible by the user and can be easily manipulated to cause advancement of suture as described herein.

Figure 5:
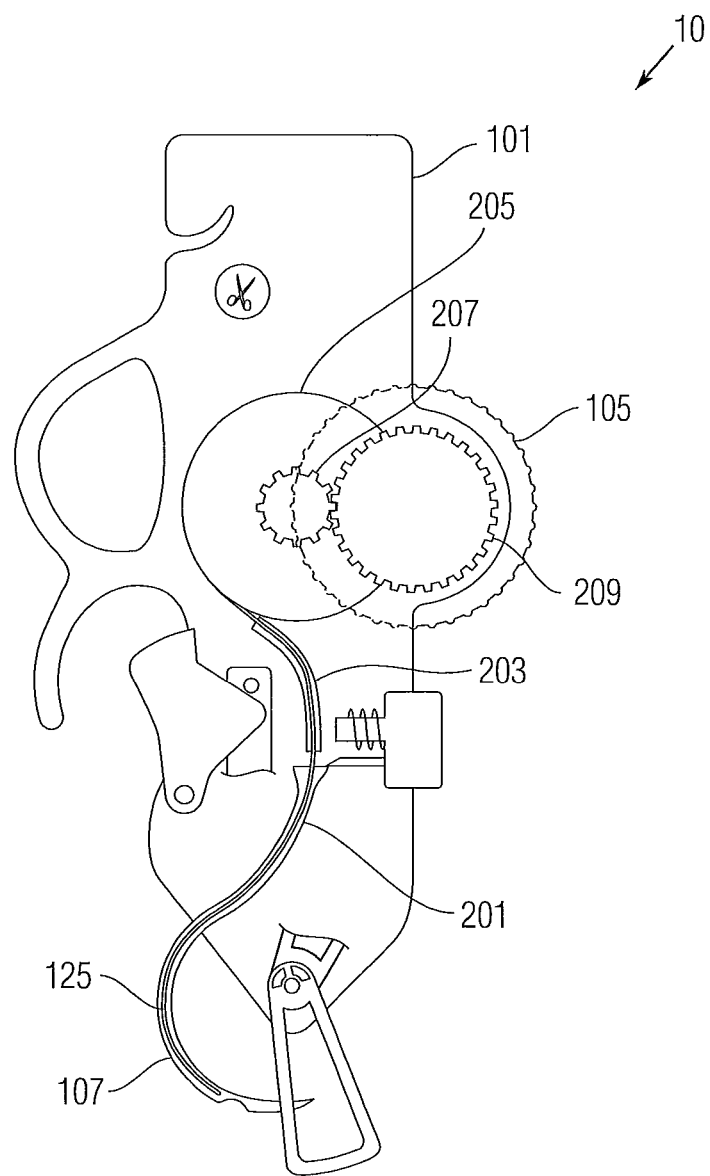
FIG. 5 is a cross-sectional view of the suturing device of FIG. 1.

The device 10 further includes a curved hollow needle 107, which is rigidly attached to the handle 101 (at a fixed location). The hollow needle 107 shown has a sharp distal point 109 (for puncturing tissue), a proximal end (not shown in FIG. 1), and a suture exit port 111 through which the suture can pass. The needle 107 is configured (disposed) in the handle 101 such that the point of the needle tip 109 can be comfortably positioned in a generally perpendicular orientation to the target tissue 20. This orientation is favorable for tissue penetration by the needle 107 although shallower approach angles to the target tissue 20 could be sufficient for penetration. As shown in FIG. 5, the hollow needle 107 can have a multi-curve construction with one curved section being external to the handle 101 and the other curved section being contained within the interior of the handle 101. An inflection point is defined along the needle at which the curvature changes between the two sections and as shown, the internal needle section can be thought of as defining a concave section (along one side), while the external needle section can be thought of as defining a convex section (along the one side).

Spring loaded safety shields 113 and 115 are configured on the device to protect the user from accidental NSIs. These shields 113, 115 are described in great detail in applicant's previous application that is incorporated herein by reference. A lockout mechanism depicted as a slideable button 117 engages one or both of the safety shields 113 and 115 such that the shields will not expose the sharp distal point of the needle 109 to the user. The lockout mechanism thus prevents the shields 113, 115 from moving (pivoting). Further, as shown in this embodiment, there is an internal suture cutter mechanism, which is portrayed as a slideable button 119 that cuts the suture to the desired length. Finally and optionally, a second suture cutter, which is capable of cutting and trimming suture that is external to the device 10, comprises an actuation button 121, a cutter guide notch 123, and an internal slideable cutting blade not shown. Further, it is easy to conceive a single cutter that accomplishes all of the cutting requirements for the device.

Figure 2:
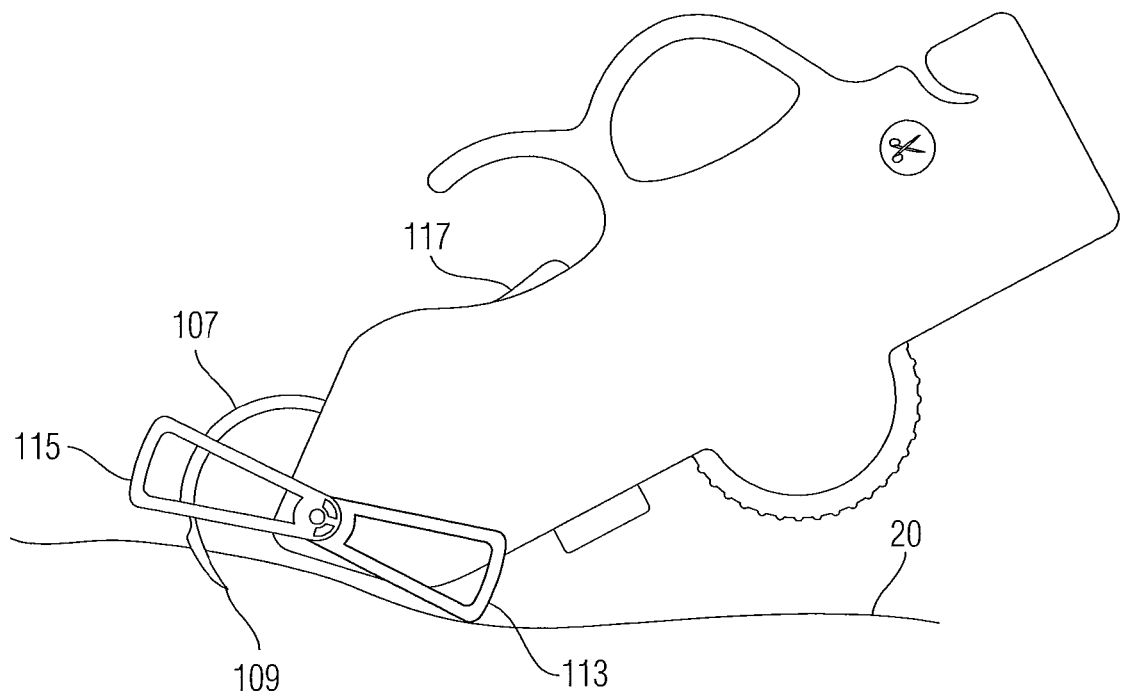
FIG. 2 is a side elevation view of the suturing device of FIG. 1 shown in a second position.

In this embodiment, one of the shields 115 can be designed such that it rotates relative to the handle 101 when the device is pressed with sufficient force against the patient's tissue 10. As shown in FIG. 2, when button 117 is pressed and unlocks safety shields 113 and 115, the device 10 and safety shield 115 can be rotated such that the needle 107 is progressively and safely exposed in order to penetrate the patient's tissue 20. The second safety shield 113 rotates relative to the first safety shield 115 and is automatically repositioned at the needle exit location of the patient's tissue 20 in order to protect the user from the needle point 109. Thus, it will be appreciated that the needle 107 itself does not move but rather the pivoting of the shields 113, 115 away from the needle point 109 exposes the needle and allows insertion into the tissue.

Figure 3:
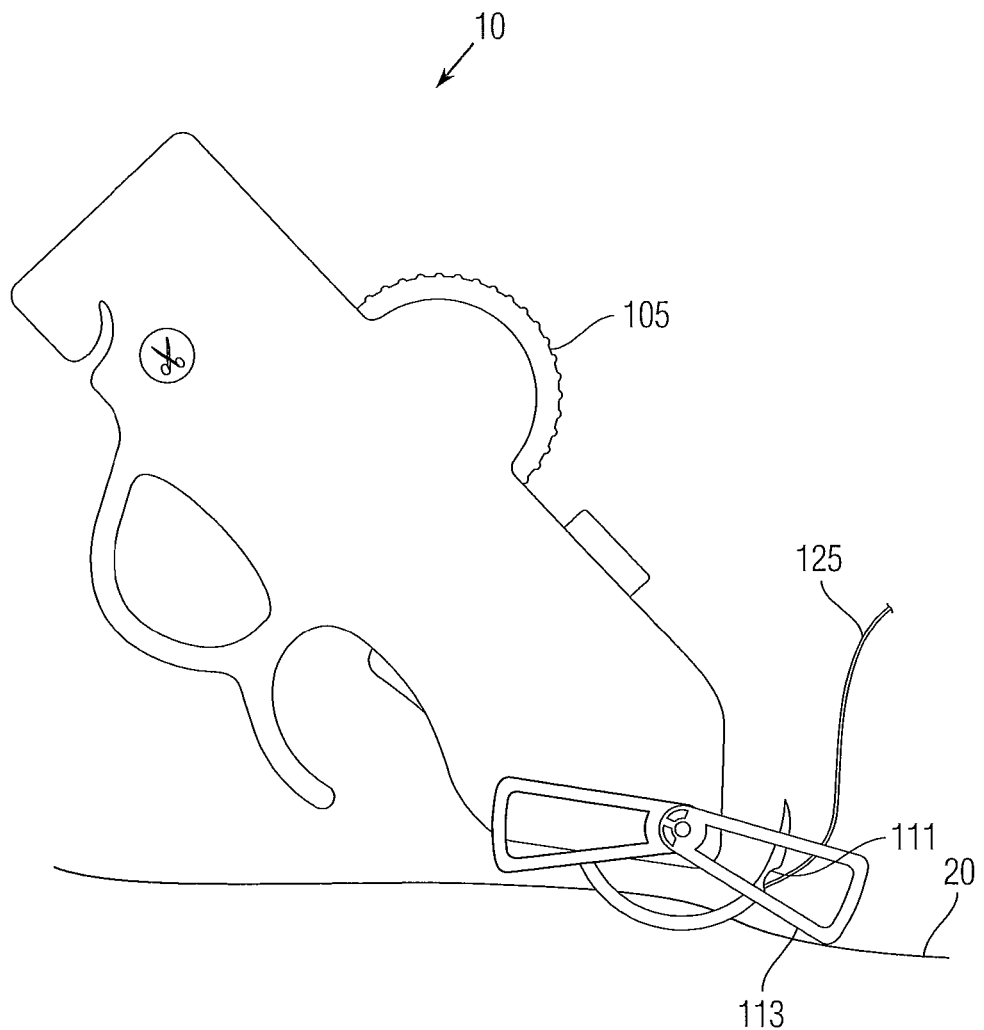
FIG. 3 is a side elevation view of the suturing device of FIG. 1 shown in a third position after the suture protrudes from the needle.

FIG. 3 depicts device 10 at or near its full rotation and the needle point 109 and the suture exit port 111 protruding from the patient's tissue 20. The safety shield 113, which is now surrounding the needle point 109, is protecting the user from contact with needle point 109. The user then rotates the actuation wheel 105, which causes the suture 125 to be dispensed from the suture exit port 111 and enables the user to grasp the suture 125 end at a safe distance from the needle point 109. The user also has the option to pull distally on the exposed suture in order to dispense additional suture from the spool without the need to actuate the wheel 105.

Figure 4:
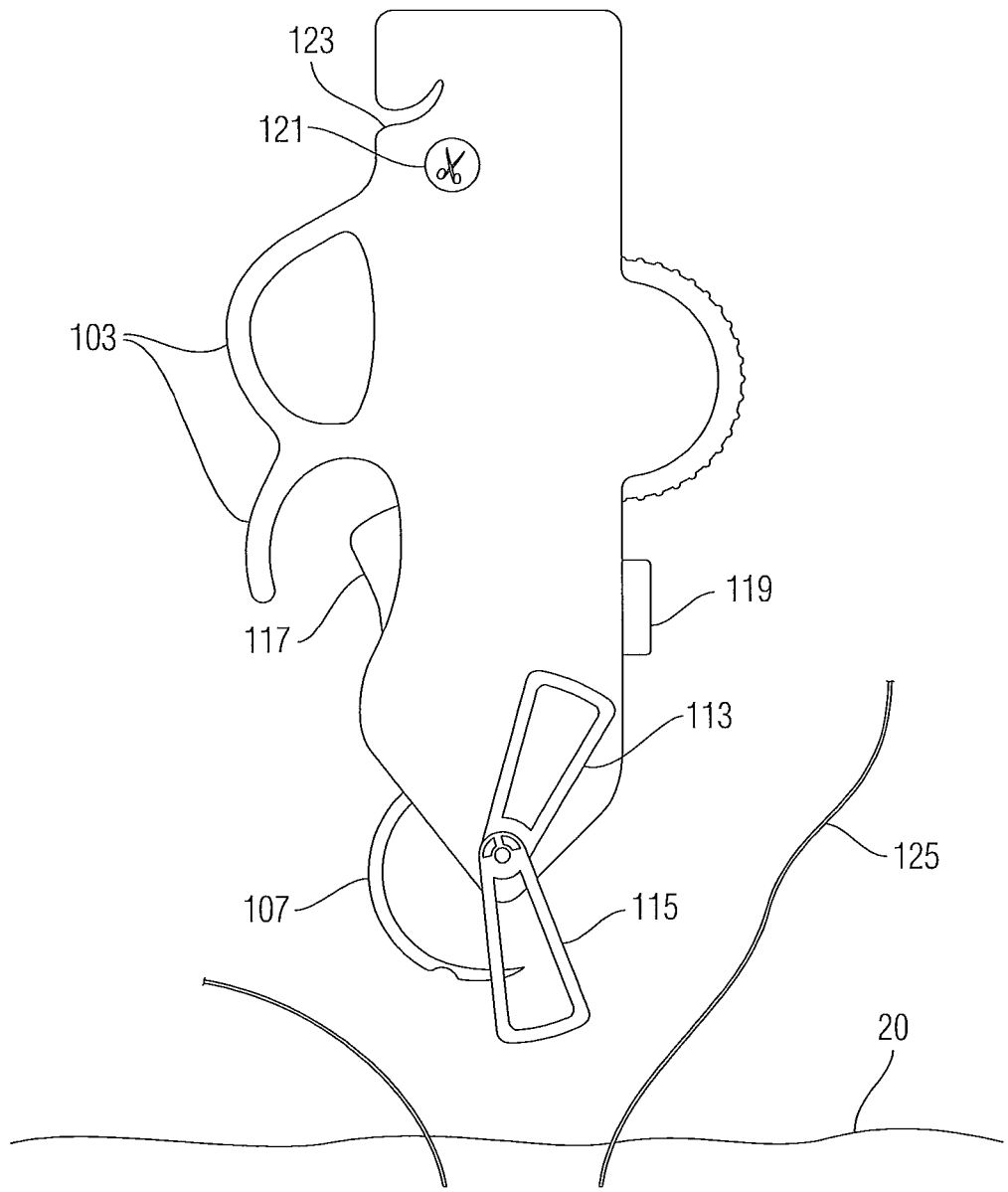
FIG. 4 is side elevation view of the suturing device of FIG. 1 shown in a fourth position after the suture has passed through the tissue.

In FIG. 4, the device 10 has been reversibly rotated such that the needle 107 has been extracted from the patient's tissue 20. At the time that the needle point 109 approaches full extraction, safety shield 115 is automatically repositioned to protect the user from the point. Once the desired length of suture 125 has been delivered, the user depresses the cutter button 119 in order to separate the suture 125 from the device 10 and the device 10 is lifted away from the patient. At this point, the device 10 is ready to deliver another suture 125 as the safety shields 113,115 and the lockout mechanism button 117 are again in their initial positions (i.e., shield 115 covers the needle point 109). The user then has the option to tie off and trim the suture 125 by guiding it into the cutter guide notch 123 and pressing the cutter actuation button 121. Additional sutures 125 can now be delivered to the patient's tissue 20. The stitches created may be continuous or interrupted. Throughout the operation of the device 10, the needle point 109 is covered by either of the safety shields 113 and 115 or embedded in the patient's tissue 20. At no time is the user exposed to the needle point 109. The construction and operation of the suture advancing mechanism is described below.

Referring now to FIG. 5, a simplified view of the inside of the suturing device 10 and handle 101 in ready mode is shown. For the sake of clarity, a number of ribs, screws, and other basic features of the handle 101 are not shown. When these features are important to the operation of the device 10, they will be described accordingly.

A closer look at the design reveals a needle 107 that it is generally hollow and extends proximally into the handle 101. As previously mentioned, the needle 107 is fixedly attached to the handle 101 and thus has a set (fixed) position. In accordance with one aspect of the present invention, the suture 125 is provided in the form of a spool or cartridge 205 that is disposed within the hollow interior of the handle body and contains a length of suture. The illustrated embodiment uses a spool 205 that has a length of suture wound therearound. Alternatively, the spool 205 can be constructed from multiple spool bodies that form an oval, for example, to minimize curling of the suture. In one embodiment, the device 10 can be in the form of a disposable product in which the spool 205 is not accessible by the end user. In this case, the pre-loaded (wound) spool 205 is disposed within the handle at the time of manufacturing and is ready for use by the end user. In yet another embodiment, the handle body 101 can be constructed such that there is access (e.g., a door) to the inside of the handle body to allow insertion and removal of the spool 205 from the inside of the handle body. In this embodiment, the spool or cartridge can thus be removed from the handle body when empty and then a new spool is inserted into the handle body. As will be appreciated below, an end of the suture can then be removed from the spool and threaded into the suture advancing mechanism as discussed below. As part of this embodiment, suture spools 205 containing suture wound around a core thereof can be commercially sold separate from the device 10. In this embodiment, the suture spool 205 can seat on a post or the like that has a degree of movement to permit the disengagement of the teeth of the gears 207, 209, thereby allowing removal of the spool 205.

The proximal end of the needle 201 is oriented in the general direction of a suture conduit 203, which may be a tube or channel that guides the suture 125 from a suture spool 205 into the needle 107. The suture conduit 203 can thus be in the form of an elongated hollow member that is formed of a rigid or semi-rigid material so that it maintains its shape. The conduit 203 can thus be shaped (e.g., curved as shown in FIG. 5) so as to cause the suture to be driven along a defined path within the handle body. As shown, one open end of the suture conduit 203 is disposed proximate the suture spool 205 to receive suture therefrom and the other open end of the suture conduit 203 is disposed proximate the proximatal end of the needle to permit the suture to be threaded into the hollow interior of the needle 107. The conduit 203 thus guides the suture between the spool 205 and the needle 107.

The conduit 203, spool 205 and wheel 105 and the linkage (e.g., gears) that couples the wheel 105 to the spool 205 thus define at least in part the suture dispensing mechanism.

Designed into the handle are supplemental features such as ribs (not shown) that ensure that the suture 125 does not lose its pathway to the distal end of the needle 107. In this embodiment, the needle 107 is rigidly fixed within the handle 101. The suture spool 205 contains and advances the suture 125 through rotation created by a pair of drive gears 207 and 209 and the actuation wheel 105. The suture spool 205 and actuation wheel 105 possess integral gears 207 and 209, respectively, which are rotatably engaged to each other. As the user turns the actuation wheel 105, the suture spool 205 rotates correspondingly and advances suture. In this embodiment, the wheel 105 is clutched (not shown) so that the spool 205 cannot rotate in the incorrect direction. Any number of conventional clutch mechanisms, such as a ratchet, can be used to accomplish this. Alternatively, the suture spool 205 can be engaged and rotated by a rack that is actuated via a button, lever, slide or similar feature located on the top or side of the handle 101. This rack can engage the spool gear 207 in order to advance the suture.

It will be appreciated that in FIG. 5, a portion of the suture spool 205 lies over a portion of the wheel 105. More specifically, the suture spool 205 can include a first section about which suture material is wound and a second section includes the gear 207. The gear 207 thus lies in a different plane than the first section that contains the wound suture material and similarly, the gear 209 of the wheel 105 lies in the same plane as the gear 207 (which is different than the plane of the wheel body 105 that is contacted by the user). Thus, in FIG. 5, the gear 207 is shown in phantom and a portion (left area) of the teeth of gear 209 and a left portion of the wheel 105 are shown in phantom to reflect the underlying nature thereof (due to the overlapping by the suture spool).

Figure 6:
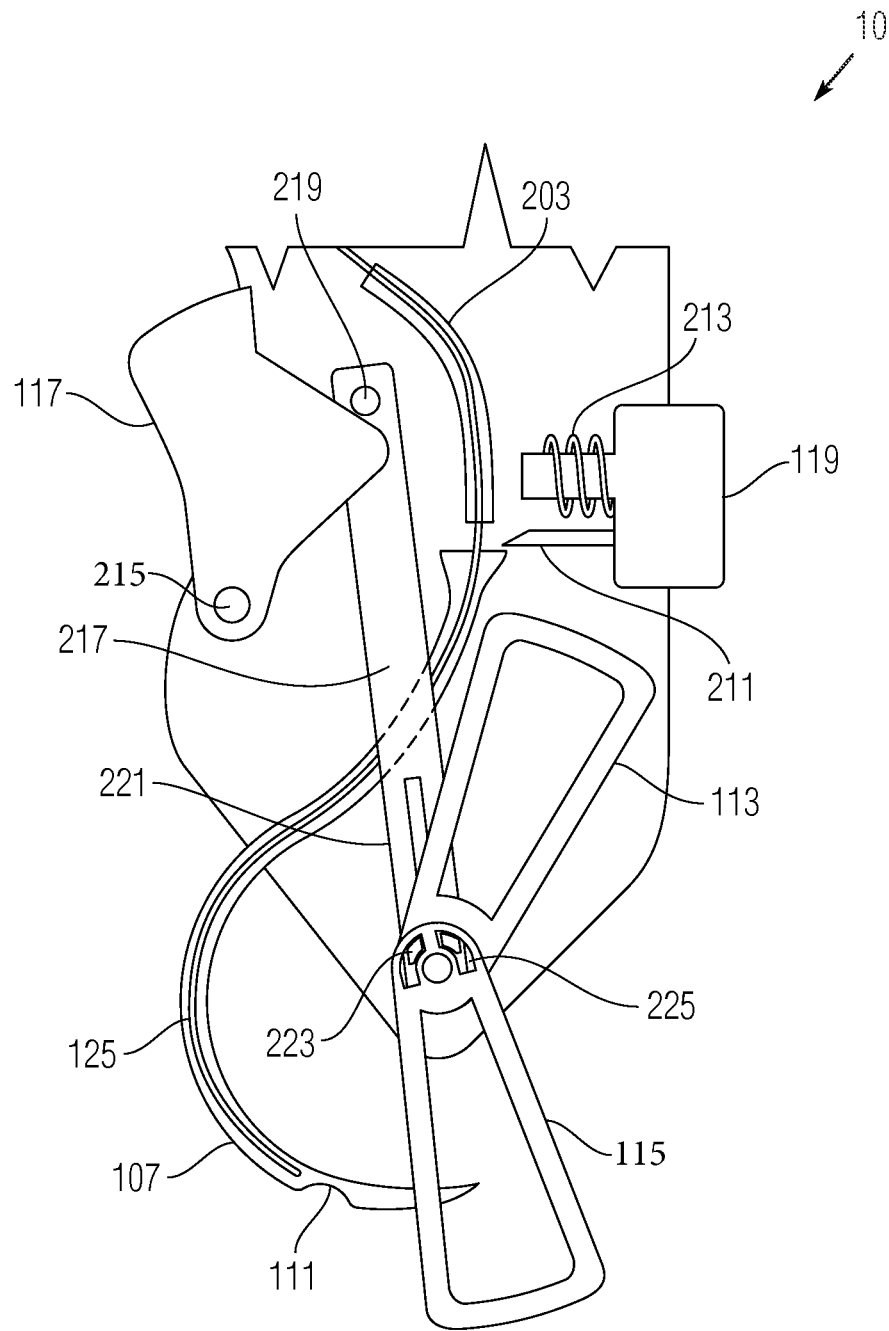
FIG. 6 is a cross-sectional view of the distal end of the suturing device of FIG. 1 prior to advancement of the suture.

FIG. 6 depicts a magnified view of the distal end of the device 10. The suture 125 can be clearly seen extending through the generally hollow needle 107 and the suture conduit 203 and terminating proximally to the suture exit port 111. The internal suture cutter mechanism is comprised of a button 119, a cutting element 211, and a return mechanism shown as a return spring 213. Further, the lockout mechanism consists of a lockout button 117, which is pivotally attached to the handle 101 by pin 215, and a lockout beam 217. The beam 217 slides generally longitudinally within a channel in the handle and alternatingly between locked and unlocked positions of safety shields 113 and 115. It also features an attached drive pin 219, legs 221, and feet 223. A spring (not shown) biases the beam distally and locks shield 115 from rotating. When button 117 is pressed, its ramp-like surface guides the drive pin 219 proximally, which in turn extracts the beam feet 223 from the lock notches 225 in safety shield 115 and allows the shield to rotate. Once the shield 115 begins to rotate, the beam feet 223 cannot reengage the shield until the shield returns to its ready mode position and the lockout button 117 is released.

Looking now at FIG. 7, the device 10 has been manipulated (in part, by user wrist motion to pivot the device relative to the tissue) such that the lockout mechanism 117 has been deactivated, the shields 113 and 115 have rotated, the needle 107 has entered and exited the patient's tissue 20, and the suture 125 has been advanced out of the suture exit port 111 by turning the actuation wheel 105. As previously disclosed, the rotation of the actuation wheel results in the spool advancing the suture though the needle 107. The suture can be effectively pushed by the spool because the suture is narrowly constrained within the suture conduit 203, hollow needle 107, and rib features (not shown) of the handle. As shown in FIG. 7, there can be a very small gap between the suture conduit and the hollow needle to allow for the cutting element 211 to cut the suture. In alternative embodiments the suture may be entirely constrained along its length, for example, by a biased telescoping suture conduit. In this case, the suture cutting element would contact and reversibly displace a portion of the telescoping suture conduit, thereby exposing the suture for cutting by the suture cutting element. As the suture cutting element returns to its original position, the bias of the telescoping suture conduit returns the conduit to its full uninterrupted length.

In this embodiment, continued rotation of the wheel 105 advances the suture through the suture conduit 203 and needle 107.

FIG. 8 represents the device 10 as it is being reversibly rotated (due to wrist motion by the user) and the needle 107 while it is in the process of being extracted from the patient's tissue 20. The distal end of suture 125 is grasped by the user in order to ensure that the suture does not withdraw from the tissue 20

FIG. 9 illustrates the progression of the needle 107 out of the patient's tissue 20 and the suture 125 left behind. Further, it shows the actuation of the internal suture cutter button 119 and the cutter blade 211 severing the suture 125. The spring 213 returns the button 119 to its origin.

And finally, in FIG. 10, the device 10 is drawn away from the patient and leaves the suture in the patient's tissue 20. The lock out button 117 has returned to its default position and safety shield 115 is restricted from rotating (thus ensuring that the sharp tip 109 is covered). The actuation wheel 105 can be rotated at this time in order to feed suture 125 into the hollow needle 107 and prepare the device 10 for delivery of an additional suture.

Alternative embodiments exist for the suture advancement and control. For example, in FIG. 11, a set of pinch rollers 301, 303 convey the suture 125 into the hollow needle 107 through the rotation of actuation wheel 105. As the wheel is turned, its integral gear 305 rotates and engages pinch roll gear 307, thus advancing the suture 125. Idler pinch roller 303 provides a counter-force to the drive pinch roller 301, which collectively supply the rotational motion to advance the suture 125. These pinch rollers can be coupled by intermeshing gear teeth or the idler pinch roller can rotate freely against the surface of the drive pinch roller. The idler pinch roller may be configured to provide a pre-determined amount of compression on the suture. The compression can be supplied by a roller surface that is elastically compliant and/or a biasing element such as a spring. For example, the idler pinch roller may be made of a compressible elastomeric material, such as a urethane foam rubber, urethane rubber, nitrile rubber, silicone, or other suitably elastic compliant material. The pinch rollers may include textured suture-engaging features, such as treads, ribs, barbs, knurls or other protrusions designed to enhance the suture gripping and advancement performance.

Furthermore, FIG. 12 depicts the handle 101 with a suture driving mechanism comprising a spring-loaded actuator 401 with compliant angled fingers 403, a U-channel 405 and a suture spool 205. The suture 125 is guided by ribs (not shown), the U-channel 405 and needle 107. In order to dispense suture 125, the user presses the spring-loaded actuator 401 such that the angled fingers 403 contact the suture in a semi-rigid manner and pushes it distally into the proximal end of the needle 107. Upon the return of the actuator 401, the orientation of the fingers 403 allows them to bend, which results in a low contact force with the suture and causes the fingers to slide past the suture. The compliant fingers of FIG. 12 are designed such that on their down stroke the fingers firmly engage the suture material while enhancing the gripping force applied to the sutures. The fingers in essence, are designed to behave as tiny cams which atraumatically grip the suture during the down-stroke of the spring-loaded actuation. On the spring-biased return stroke of the actuator the fingers are designed to easily deflect in the opposite direction and glide past the suture without drawing it in the reverse direction. The user may activate the actuator multiple times in order to dispense additional suture.

In this embodiment, the linear motion of actuator 401 is transmitted into advancement of the suture into and through the hollow needle.

The general form of the device as illustrated in FIG. 12 could be configured with alternative mechanisms to achieve the same end. For example, a device similar to the one shown in FIG. 12, could comprise a spring loaded actuator that drives a spring loaded collet designed for suture advancement.

Looking now at the safety shields 113 and 115, FIGS. 13 and 14 illustrate the front and back views two piece safety apparatus that is described in this invention. The first safety shield 115 is rotatably coupled to the device handle 101 by an axle 501 and a torsion spring 503 or other suitable means. The first safety shield is also rotatably coupled to a second safety shield 113 by a torsion spring 505 or other suitable means. The spring-loaded engagement between the first safety shield and the handle permits the user to rotate this shield 115 relative to the handle and to safely penetrate the patient's tissue with the needle 107. The spring-loaded engagement between the first safety shield 115 and the second safety shield 113 forces the latter shield to follow the rotational path of the former while simultaneously providing flexibility between the two shields. This flexibility enables the shields to adapt to variable topographies (e.g., tissue, catheter hubs) and still protect the user from the point 109 of the needle throughout the operation. In another contemplated embodiment, the shields may be constructed as a single piece that features an integral flexible portion that allows for a similar adaptation to variable topographies. An additional feature of the safety shield(s) provides the user with the ability to precisely deliver the needle to the patient. This feature may be a protrusion on one of the shields that, for example, aligns the needle to the suture hole of a catheter hub. This feature may also be a ring, semi-circular structure, or visible mark on the shield that helps the user to more clearly visualize the desired needle penetration and/or exit sites upon the tissue. This feature is described in detail and illustrated in applicant's previous application which is incorporated herein by reference.

The shields 113 and 115 may also be designed in a specific geometric manner such that one or both of them guide or predetermine the needle trajectory through the patient's tissue. The shields, when placed on the tissue, would guide the user's rotational hand motion such that the needle would initially penetrate the tissue in an essentially perpendicular orientation and is subsequently oriented into a more obtuse orientation that facilitates the advancement of the curved needle through the remaining tissue. This gentle compound rotating motion is representative of that which is currently employed by healthcare personnel when manually driving needles through tissue. In practical terms, it minimizes the risk of excessively penetrating the patient's tissue.

Alternatively, the shield(s) can be constructed from a frame-work of formed wire or plastic yet operates similarly to the shields depicted in FIGS. 13 and 14. It may be formed of one or more components and its rotation may be constrained by a spring or other suitable means. Further, the spring element may be integral to the framework, e.g., a wire form constructed of spring tempered steel or nickel titanium alloy which possess substantial elasticity. It features a spring bias that predisposes the shield towards covering the needle point 109 when the device is in its ready to penetrate configuration.

Finally, a suture cutter 511 that is integral to the handle would provide the user with a means to cut and trim suture 125 during the procedure. As depicted in FIG. 15, the cutter is an internal dynamic shearing apparatus, i.e., scissors or slideable blade(s) that would require the user to press or slide a button 121 in order to activate the blade 513 to cut the suture 125. The button 121 is connected to a means that translates the blade 513 across the suture 125 and into a slot that is functionally narrow, providing a holding surface for the suture and allowing only the blade to travel therethrough. This means could be a slideable track if the button were to slide in the cutting direction of the blade, or a pair of matched ramps that would convert the vertical motion of the depressed button to a horizontal motion of a cutting blade. A spring or other suitable means (not shown) would return the button 121 to its original position. Further, the suture 125 would be positioned in a notch, slot, or hole 123 on the outer surface of the housing 101 in order for the user to cut it.

Alternatively shown in FIG. 16, the cutter is a simple apparatus such as a static cutting blade 515 located near the exterior surface of the handle 101. The blade 515 would be affixed in a narrowing, crevice-like feature 123 that is sized so that the suture 125 may be drawn across the blade's sharp edge in order to cut it, however, direct access to the blade by the user is not possible due to the crevice's narrow pathway. These cutting mechanisms would reduce or eliminate the need for the user to provide a pair of scissors for the suturing procedure.

The devices of the present invention provide a number of advantageous features/mechanisms including but not limited to: (1) wrist rotation for delivering needle and extracting needle (pronation and supination beginning and ending with the device being at acute angles relative to the tissue); (2) right and left handedness equivalence of a hollow needle/suture without modification or reconfiguration of the device; (3) internal suture cutter that cuts the suture, retracts, and allows the proximal cut end of the suture to advance distally for a subsequent suture delivery; (4) safety guards with a lock-out mechanism; (5) suture cutter for trimming tied suture; (6) suture advancement and payout means. In addition, the device is configured to allow the user to manually pass said suturing needle through tissue at a predetermined penetration depth by employing a device-guided rotational motion of the hand. The device is further configured to deliver said suture into tissue at a penetration depth of 2 to 20 millimeters and a span of 2 to 30 millimeters.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for suturing tissue comprising:
a handle comprising a proximal end and a distal end;
a generally hollow suturing needle comprising a pointed distal end, an opposite proximal end and an inner lumen having an suture exit port through which a suture material exits;
a suture dispensing mechanism disposed within the handle and including a first actuator which when manipulated by a user is configured to advance suture material within the handle such that the suture material is guided into the inner lumen of the hollow suturing needle and exits through the suture exit port, wherein the first actuator is accessible to a user along one side of the handle to allow the first actuator to be contacted and driven by the user to cause the suture material to be advanced through and then exit from the hollow suturing needle;
a first suture cutter mechanism for cutting the suture material internally within the handle at a location proximal to an entrance into the inner lumen of the suturing needle, the first suture cutter mechanism including a second actuator and a first cutting element coupled thereto, the first cutting element being positioned such that upon actuation of the second actuator, the first cutting element is advanced into contact with the suture material, thereby cutting the suture material; and
a safety mechanism shielding at least a portion of the needle;
wherein the suture dispensing mechanism comprises a manually driven mechanism and includes a suture spool that contains wound suture material, the suture spool including a second gear that is in direct contact with a first gear of the first actuator, the suture spool being disposed completely within an interior space of the handle, wherein the advanced suture material travels directly from the suture spool toward a suture guide without contacting the first actuator.

2. The device in claim 1, wherein the safety mechanism is pivotally attached to the handle and the device is configured to allow the user to manually pass the suturing needle through tissue at variable penetration depths by employing a rotational motion of the user's hand.

3. The device of claim 1, wherein the suture dispensing mechanism is configured such that manual movement of an accessible portion of the first actuator by the user is translated into rotation of the suture spool and the suture material is advanced within the handle, whereby continued rotation of the suture spool results in the suture material being guided into the inner lumen of the hollow suturing needle and exiting through the suture exit port.

4. The device of claim 3, wherein the first actuator comprises a wheel that is rotatably coupled to the handle and which is at least partially accessible by the user to permit rotation of the wheel.

5. The device of claim 3, wherein the handle is constructed to permit a user to remove one suture spool and insert a replacement suture spool.

6. The device of claim 3, wherein the suture guide comprises a suture conduit member that is fixedly attached to the handle and has an inner lumen through which the suture passes, the suture conduit member being disposed between the suture spool and the proximal end of the needle with the cutting element of the first suture cutter mechanism being disposed between the suture conduit and the proximal end of the needle.

7. The device of claim 6, wherein a distal end of the inner lumen of the suture conduit is axially aligned with the inner lumen of the needle at the proximal end thereof.

8. The device of claim 1, further including a second suture cutter mechanism for cutting suture material that is located external to the handle, the second suture cutter mechanism including a third actuator and a second cutting element coupled thereto and a slot formed and open along a side of the handle to receive the suture material, the second suture cutter mechanism being disposed proximal to the proximal end of the needle, the second cutting element being positioned such that upon actuation of the third actuator, the second cutting element is advanced into contact with the suture material that is disposed within the slot, thereby cutting the suture material.

9. The device of claim 8, wherein the second suture cutter mechanism is disposed between the suture dispensing mechanism and the proximal end of the handle.

10. A device for suturing tissue comprising:
a handle comprising a proximal end and a distal end;
a generally hollow suturing needle comprising a pointed distal end, an opposite proximal end and an inner lumen having an suture exit port through which the suture exits;
a suture dispensing mechanism disposed within the handle and including a first actuator which when manipulated by a user is configured to advance suture material within the handle such that the suture material is guided into the inner lumen of the hollow suturing needle and exits through the suture exit port; and
a safety mechanism shielding at least a portion of the needle;
wherein the safety mechanism comprises a pair of safety guards that are pivotally attached to the handle, the guards being configured to shroud the needle during needle penetration and when the needle exits tissue.

11. A device for suturing tissue comprising:
a handle comprising a proximal end and a distal end;
a generally hollow suturing needle comprising a pointed distal end, an opposite proximal end and an inner lumen having an suture exit port through which a suture material exits;
a suture dispensing mechanism disposed within the handle and including a first actuator which when manipulated by a user is configured to advance suture material within the handle such that the suture material is guided into the inner lumen of the hollow suturing needle and exits through the suture exit port;
a first suture cutter mechanism for cutting the suture material internally within the handle at a location proximal to an entrance into the inner lumen of the suturing needle, the first suture cutter mechanism including a second actuator and a first cutting element coupled thereto, the first cutting element being positioned such that upon actuation of the second actuator, the first cutting element is advanced into contact with the suture material, thereby cutting the suture material;
a safety mechanism shielding at least a portion of the needle; and
a lockout mechanism including a lockout deactivating element for deactivating the lockout mechanism, a lockout element, a lockout actuator, and a means to connect the lockout actuator to the lockout element, wherein the lockout element is configured to prevent the safety mechanism from exposing the pointed distal end until the lockout mechanism is deactivated.

12. The lockout mechanism in claim 11, wherein said lockout element is configured with a protrusion that reversibly engages the safety mechanism.

13. The lockout element in claim 11, wherein said lockout element lockably engages the safety mechanism only when the safety mechanism is in its original ready position.

14. A device for suturing tissue comprising:
a handle comprising a proximal end and a distal end, the handle being rotatable about a first axis located proximate the distal end;
a generally hollow suturing needle comprising a pointed distal end, an opposite proximal end and an inner lumen having an suture exit port through which a suture material exits, wherein the suturing needle is fixedly attached to the handle and is curved such that the suturing needle extends across a width of the distal end of the handle so as to position the suture exit port at a location that is distal to the distal end of the handle;
a suture dispensing mechanism disposed within the handle and including an actuator which when manipulated by a user is configured to advance the suture material within the handle such that the suture material is guided into the inner lumen of the hollow suturing needle and exits through the suture exit port; and
a safety mechanism shielding at least a portion of the needle, wherein the safety mechanism comprises a pair of safety guards that are pivotally attached to the handle and rotate about the first axis, the guards being configured to shroud the needle during needle penetration and when the needle exits tissue;
wherein in a first operating position prior to insertion of the suturing needle into the tissue, the handle is positioned at a first acute angle relative to a tissue surface and the device is configured such that movement of the handle about the first axis from the first position to a second operating position in which the handle is positioned at a second acute angle relative the tissue surface causes the suturing needle to be driven into and through the tissue;
wherein the first axis is perpendicular to a longitudinal axis of the handle that extends from the proximal end to the distal end.

* * * * *